United States Patent
Andrews et al.

(10) Patent No.: US 7,279,328 B1
(45) Date of Patent: *Oct. 9, 2007

(54) METHODS AND COMPOSITIONS FOR MODULATING TELOMERASE REVERSE TRANSCRIPTASE (TERT) EXPRESSION

(75) Inventors: William H. Andrews, Reno, NV (US); Christopher A. Foster, Carmichael, CA (US); Stephanie Fraser, Sparks, NV (US); Hamid Mohammadpour, Reno, NV (US); Laura Briggs, Reno, NV (US)

(73) Assignee: Sierra Sciences, Inc., Reno, NV (US)

(*) Notice: Subject to any disclaimer, the term of this patent is extended or adjusted under 35 U.S.C. 154(b) by 35 days.

This patent is subject to a terminal disclaimer.

(21) Appl. No.: 10/826,466

(22) Filed: Apr. 16, 2004

Related U.S. Application Data

(63) Continuation of application No. 10/675,794, filed on Sep. 29, 2003, now abandoned.

(60) Provisional application No. 60/415,007, filed on Sep. 30, 2002.

(51) Int. Cl.
*C12N 5/00* (2006.01)

(52) U.S. Cl. .......................................... 435/325; 435/6

(58) Field of Classification Search .................. None
See application file for complete search history.

(56) References Cited

FOREIGN PATENT DOCUMENTS

| WO | WO 02/16657 | 2/2002 |
|----|-------------|--------|
| WO | WO 02/16658 | 2/2002 |

OTHER PUBLICATIONS

Nozawa, K. et al. J Biol Chem 276(25):22016-22023, 2001.*
Horikawa, I. et al. PNAS 102(51):18437-18442, 2005.*
Oh, S. et al. J Biol Chem 274(52):37473-37478, 1999.*
Oh, S. et al. Oncogene 19:1485-1490, 2000.*

* cited by examiner

*Primary Examiner*—Anne-Marie Falk
*Assistant Examiner*—Marcia S. Noble
(74) *Attorney, Agent, or Firm*—Bret E. Field; David C. Scherer; Bozicevic, Field & Francis LLP

(57) ABSTRACT

Methods and compositions are provided for modulating, e.g., increasing or decreasing, the expression of telomerase reverse transcriptase (TERT). In the subject methods, the binding interaction of the GC-Box 5 repressor site with a repressor protein (or protein complex including the same) is modulated to achieve the desired change in TERT expression. The subject methods and compositions find use in a variety of different applications, including the immortalization of cells, the production of reagents for use in life science research, therapeutic applications; therapeutic agent screening applications; and the like.

11 Claims, 1 Drawing Sheet

FIGURE 1

Annotated Minimal Promoter (SEQ ID NO:02)

```
                   -258                 E-BOX
                    |                  ******
         CGCGTGCTAGCCCGGGCTCGAGCCAGGACCGCGCTCCCCACGTGGCGGAGGGACTGGGGA
                              =========                         ==
                                 TF-1

SP1             SP1
                                     ********        *******
                                     GC-Box 1        GC-Box 2
                                   *************    **********
-220     CCCGGGCACCCGTCCTGCCCCTTCACCTTCCAGCTCCGCCTCCTCCGCGCGGACCCCGCC
         ========  ==========         ===========          =======
           TF-2       TF-3                TF-4               TF-5

**                    SP1             SP1
                                  ********        ********
                                  GC-Box 3        GC-Box 4
                                *************    **********
         ****
-160     CCGTCCCGACCCCTCCCGGGTCCCCGGCCCAGCCCCCTCCGGGCCCTCCCAGCCCCTCCC
         ===                    ==========
                                    TF-6         ===========
                                                     TF-7

SP1
                     ********
                     GC-Box 5
              ***   *************
-100     CTTCCTTTCCGCGGCCCCGCCCTCTCCTCGCGGCGCGAGTTTCAGGCAGCGCTGCGTCCT
              ============                                 =======
                   TF-9                                      TF-11
              Key Activator E-Box
             ******
-40      GCTGCGCACGTGGGAAGCCCTGGCCCCGGCCACCCCGCGAATTCGCCCACCATG   (SEQ ID NO:02)
         ===         ==========
                        TF-12
```

METHODS AND COMPOSITIONS FOR MODULATING TELOMERASE REVERSE TRANSCRIPTASE (TERT) EXPRESSION

CROSS-REFERENCE TO RELATED APPLICATIONS

This is a continuation of application Ser. No. 10/675,794, filed Sep. 29, 2003, now abandoned which claims priority to the filing date of the U.S. Provisional Patent Application Ser. No. 60/415,007 filed Sep. 30, 2002; the disclosure of which is herein incorporated by reference.

INTRODUCTION

1. Field of the Invention

The field of this invention is the telomerase reverse transcriptase gene, specifically the regulation of the expression thereof.

2. Background of the Invention

Telomeres, which define the ends of chromosomes, consist of short, tandemly repeated DNA sequences loosely conserved in eukaryotes. Human telomeres consist of many kilobases of $(TTAGGG)_n$ together with various associated proteins. Small amounts of these terminal sequences or telomeric DNA are lost from the tips of the chromosomes during S phase because of incomplete DNA replication. Many human cells progressively lose terminal sequence with cell division, a loss that correlates with the apparent absence of telomerase in these cells. The resulting telomeric shortening has been demonstrated to limit cellular lifespan.

Telomerase is a ribonucleoprotein that synthesizes telomeric DNA. Human telomerase is made up of two components: (1) an essential structural RNA (TER) (where the human component is referred to in the art as hTER); and (2) a catalytic protein (telomerase reverse transcriptase or TERT) (where the human component is referred to in the art as hTERT). Telomerase works by recognizing the 3' end of DNA, e.g., telomeres, and adding multiple telomeric repeats to its 3' end with the catalytic protein component, e.g., hTERT, which has polymerase activity, and hTER which serves as the template for nucleotide incorporation. Of these two components of the telomerase enzyme, both the catalytic protein component and the RNA template component are activity limiting components.

Because of its role in cellular senescence and immortalization, there is much interest in the development of protocols and compositions for regulating expression of telomerase.

Relevant Literature

WO 02/16657 and WO 02/16658 and the references cited therein

SUMMARY OF THE INVENTION

Methods and compositions are provided for modulating, e.g., increasing or decreasing, the expression of telomerase reverse transcriptase (TERT). In the subject methods, the binding interaction of the GC-Box 5 repressor site with a repressor protein (or protein complex including the same) is modulated to achieve the desired change in TERT expression. The subject methods and compositions find use in a variety of different applications, including the immortalization of cells, the production of reagents for use in life science research, therapeutic applications; therapeutic agent screening applications; and the like.

BRIEF DESCRIPTION OF THE FIGURES

FIG. 1 provides the annotated TERT minimal promoter.

DESCRIPTION OF THE SPECIFIC EMBODIMENTS

Methods and compositions are provided for modulating, e.g., increasing or decreasing, the expression of telomerase reverse transcriptase (TERT). In the subject methods, the binding interaction of the GC-Box 5 repressor site with a repressor protein (or protein complex including the same) is modulated to achieve the desired change in TERT expression. The subject methods and compositions find use in a variety of different applications, including the immortalization of cells, the production of reagents for use in life science research, therapeutic applications; therapeutic agent screening applications; and the like.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the elements that are described in the publications which might be used in connection with the presently described invention.

In further describing the subject invention, the methods and compositions of the invention are described first in greater detail, followed by a review of the various applications in which the subject invention finds use.

Methods

As summarized above, the subject invention provides methods and compositions for modulating expression of TERT. In the subject methods, TERT expression repression is modulated by modulating the TERT expression repression activity of a "GC-box 5" repressor binding site, where modulating includes both increasing and decreasing the expression repressive activity of the target GC-box 5 repressor binding site. As such, in certain embodiments, methods of increasing expression of TERT are provided, while in other embodiments, methods of decreasing expression of TERT are provided, where in both embodiments the modulation of expression is accomplished by modulating the repressor activity of the GC-Box 5 repressor site.

GC-Box 5 Repressor Site

In certain embodiments, the GC-Box 5 repressor site whose activity is modulated in the subject methods comprises a sequence of nucleotide residues that is bound by a repressor protein, either alone or in combination with one or more additional proteins, cofactors, e.g., a Site C repressor protein, as described in U.S. patent application Ser. Nos. 09/932,581; PCT/US02/07918; and 10/177,744; the disclosures of which are herein incorporated by reference. As such, the GC-Box 5 repressor site is a site that binds a complex of one or more proteins/factors, where binding of the complex to this site, and, other sites (such as the Site C site described in the above patent applications) results in inhibition of TERT transcription.

The target GC-Box 5 repressor site typically ranges in length from about 1 base, usually at least about 5 bases and more usually at least about 15 bases, to a length of about 25 bases or longer, e.g., 50, 75 or 100, etc. In many embodiments, the length of the target GC-Box 5 repressor site/domain ranges in length from about 1 to about 50 bases, usually from about 5 to about 45 bases.

By GC-Box 5 repressor binding site is meant the site of the TERT promoter that binds to a repressor protein or transcription factor (or complex thereof), where binding of the repressor protein/complex to the GC-Box 5 repressor binding site results in repression of TERT expression. The subject GC-Box 5 binding site binds to a GC-Box 5 transcription repression factor (i.e., the GC-Box 5 binding site has a sequence that is recognized by an GC-Box 5 repressor protein).

The subject GC-Box 5 repressor binding site is located in the region from about —89 to about —76, of the TERT promoter, i.e., about —89 to about —76 relative to the "A" of the telomerase ATG codon. The GC-Box 5 binding site sequence is CGGCCCCGCCCTCT (SEQ ID NO:01).

Also of interest are GC-Box 5 sites that have a sequence that is substantially the same as, or identical to, the GC-Box 5 repressor binding site sequence as described above, e.g., SEQ ID NO: 01. A given sequence is considered to be substantially similar to this particular sequence if it shares high sequence similarity with the above described specific sequences, e.g. at least 75% sequence identity, usually at least 90%, more usually at least 95% sequence identity with the above specific sequences. Sequence similarity is calculated based on a reference sequence, which may be a subset of a larger sequence. A reference sequence will usually be at least about 5 nt long, more usually at least about 10 nt long, and may extend to the complete sequence that is being compared. Algorithms for sequence analysis are known in the art, such as BLAST, described in Altschul et al. (1990), *J. Mol. Biol.* 215:403-10 (using default settings, i.e. parameters w=4 and T=17). Of particular interest in certain embodiments are nucleic acids of substantially the same length as the specific nucleic acid identified above, where by substantially the same length is meant that any difference in length does not exceed about 20 number %, usually does not exceed about 10 number % and more usually does not exceed about 5 number %; and have sequence identity to this sequence of at least about 90%, usually at least about 95% and more usually at least about 99% over the entire length of the nucleic acid.

Also of interest are nucleic acids that represent a modified or altered GC-Box 5 site, e.g., where the site includes one or more deletions or substitutions as compared to the above specific GC-Box 5 sequences, including a deletion or substitution of a portion of the GC-Box 5 repressor binding site, e.g., a deletion or substitution of at least one nucleotide, e.g., a deletion or substitution of —80C, such as —80C→A.

Modulating TERT Expression

The subject invention provides methods of modulating, including both enhancing and repressing, TERT expression. As such, methods of both increasing and decreasing TERT expression are provided. In many embodiments, such methods are methods of modulating the binding interaction and resultant GC-Box 5 TERT expression repression activity between the GC-Box 5 site in a minimal TERT promoter and a GC-Box 5 repressor protein/complex, where in many embodiments the GC-Box 5 repressor protein/complex is a complex of two or more proteins that includes a GC-Box 5 binding protein and a Site C repressor protein, e.g., as described in U.S. patent application Ser. Nos. 09/932,581; PCT/US02/07918; and 10/177,744; the disclosures of which are herein incorporated by reference.

In modulating TERT expression, the interaction between the GC-Box 5 repressor site and its repressor protein/complex can be modified directly or indirectly. An example of direct modification of this interaction is where the binding of the repressor protein/complex to the target sequence is modified by an agent that directly changes how the repressor protein/complex binds to the GC-Box 5 sequence, e.g., by occupying the DNA binding site of the repressor protein/complex, by binding to the GC-Box 5 sequence thereby preventing its binding to the repressor protein/complex, etc. An example of indirect modification is modification/modulation of the GC-Box 5 repressive activity via disruption of a binding interaction between the repressor protein/complex and one or more cofactors (such as a Site C binding protein as described above) (or further upstream in the chain of interactions, such as cofactors that interact with the GC-Box 5 binding protein to make it a repressor, as described above) such that the repressive activity is modulated, by modification/alteration of the GC-Box 5 DNA binding sequence such that binding to the repressor protein is modulated, etc.

Enhancing TERT Expression

Methods are provided for enhancing TERT expression. By enhancing TERT expression is meant that the expression level of the TERT coding sequence is increased by at least about 2-fold, usually by at least about 5-fold and sometimes by at least 25-, 50-, 100-fold and in particular about 300-fold or higher, as compared to a control, i.e., expression from an expression system that is not subjected to the methods of the present invention. Alternatively, in cases where expression of the TERT gene is so low that it is undetectable, expression of the TERT gene is considered to be enhanced if expression is increased to a level that is easily detectable.

In these methods, GC-Box 5 repression of TERT expression is inhibited. By inhibited is meant that the repressive activity of the TERT GC-Box 5 repressor binding site/repressor protein/complex interaction with respect to TERT expression is decreased by a factor sufficient to at least provide for the desired enhanced level of TERT expression, as described above. Inhibition of GC-Box 5 transcription repression may be accomplished in a number of ways, where representative protocols for inhibiting this TERT expression repression are now provided.

One representative method of inhibiting repression of transcription is to employ double-stranded, i.e., duplex, oligonucleotide decoys for the GC-Box 5 repressor protein/complex, which bind to the GC-Box 5 repressor protein/complex and thereby prevent the GC-Box 5 repressor protein/complex from binding to its target GC-Box 5 site in the TERT promoter, e.g., the GC-Box 5 site of the TERT minimal promoter. These duplex oligonucleotide decoys have at least that portion of the sequence of the TERT GC-Box 5 site required to bind to the repressor protein/complex and thereby prevent its binding to the GC-Box 5 site. In many embodiments, the subject decoy nucleic acid molecules include a sequence of nucleotides that is the same as a sequence found in SEQ ID NO: 01. In other embodiments, the subject decoy nucleic acid molecules include a sequence of nucleotides that is substantially the same as or identical to a sequence found in SEQ ID NO: 01; where the terms substantially the same as and identical thereto in relation to nucleic acids are defined below. In many embodiments, the length of these duplex oligonucleotide decoys ranges from about 5 to about 5000, usually from about 5 to about 500 and more usually from about 10 to about 50 bases. In using such oligonucleotide decoys, the decoys are placed into the environment of the GC-Box 5 site and its GC-Box 5 repressor protein/complex, resulting in de-repression of the transcription and expression of the TERT coding sequence. Oligonucleotide decoys and methods for their use and administration are further described in general terms in Morishita et al., Circ Res (1998) 82 (10):1023-8. These oligonucleotide decoys generally include a TERT GC-Box 5 repressor binding site recognized by the GC-Box 5 repressor protein/complex, including the specific regions detailed above, where these particular embodiments include nucleic acid compositions of the subject invention, as described in greater detail below.

Instead of the above-described decoys, other agents that disrupt binding of the GC-Box 5 repressor protein/complex to the target TERT GC-Box 5 repressor binding site and thereby inhibit its expression repression activity may be employed. Other agents of interest include, among other types of agents, nucleic acid agents employed in the targeted disruption of the GC-Box 5 repressor domain (as described below), small molecules that bind to the GC-Box 5 repressor protein/complex and inhibit its binding to the GC-Box 5 repressor region. Alternatively, agents that bind to the GC-Box 5 sequence and inhibit its binding to the GC-Box 5 repressor protein/complex are of interest. Alternatively, agents that disrupt GC-Box 5 repressor protein-protein interactions with cofactors, e.g., cofactor binding, and thereby inhibit GC-Box 5 repression are of interest.

Naturally occurring or synthetic small molecule compounds of interest include numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Such molecules may be identified, among other ways, by employing the screening protocols described below. Other agents include "designer" DNA binding proteins that bind GC-Box 5 (without causing repression) and prevent the GC-Box 5 repressor protein/complex from binding.

In yet other embodiments, expression of the GC-Box 5 repressor protein is inhibited. Inhibition of GC-Box 5 repressor protein expression may be accomplished using any convenient means, including administration of an agent that inhibits GC-Box 5 repressor expression (e.g., antisense agents), inactivation of the GC-Box 5 repressor gene, e.g., through recombinant techniques, etc.

For example, antisense molecules can be used to downregulate expression of the target repressor protein in cells. The anti-sense reagent may be antisense oligodeoxynucleotides (ODN), particularly synthetic ODN having chemical modifications from native nucleic acids, or nucleic acid constructs that express such anti-sense molecules as RNA. The antisense sequence is complementary to the mRNA of the targeted repressor protein, and inhibits expression of the targeted repressor protein. Antisense molecules inhibit gene expression through various mechanisms, e.g. by reducing the amount of mRNA available for translation, through activation of RNAse H, or steric hindrance. One or a combination of antisense molecules may be administered, where a combination may comprise multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996), Nature Biotechnol. 14:840-844).

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides may be chemically synthesized by methods known in the art (see Wagner et al. (1993), supra, and Milligan et al., supra.) Preferred oligonucleotides are chemically modified from the native phosphodiester structure, in order to increase their intracellular stability and binding affinity. A number of such modifications have been described in the literature, which alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH$_2$-5'-O-phosphonate and 3'-NH-5'-O-phosphoroamidate. Peptide nucleic acids replace the entire ribose phosphodiester backbone with a peptide linkage. Sugar modifications are also used to enhance stability and affinity. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

As an alternative to anti-sense inhibitors, catalytic nucleic acid compounds, e.g. ribozymes, anti-sense conjugates, etc. may be used to inhibit gene expression. Ribozymes may be synthesized in vitro and administered to the patient, or may be encoded on an expression vector, from which the ribozyme is synthesized in the targeted cell (for example, see International patent application WO 9523225, and Beigelman et al. (1995), *Nucl. Acids Res.* 23:4434-42). Examples of oligonucleotides with catalytic activity are described in WO 9506764. Conjugates of anti-sense ODN with a metal complex, e.g. terpyridylCu(II), capable of mediating mRNA hydrolysis are described in Bashkin et al. (1995), Appl. Biochem. Biotechnol. 54:43-56.

In another embodiment, the repressor protein gene is inactivated so that it no longer expresses a functional repressor protein. By inactivated is meant that the repressor gene, e.g., coding sequence and/or regulatory elements thereof, is genetically modified so that it no longer expresses functional repressor protein. The alteration or mutation may take a number of different forms, e.g., through deletion of one or more nucleotide residues in the repressor region, through exchange of one or more nucleotide residues in the repressor region, and the like. One means of making such alterations in the coding sequence is by homologous recombination. Methods for generating targeted gene modifications through homologous recombination are known in the art, including those described in: U.S. Pat. Nos. 6,074,853; 5,998,209; 5,998,144; 5,948,653; 5,925,544; 5,830,698; 5,780,296; 5,776,744; 5,721,367; 5,614,396; 5,612,205; the disclosures of which are herein incorporated by reference.

The above-described methods of enhancing TERT expression find use in a number of different applications. In many applications, the subject methods and compositions are employed to enhance TERT expression in a cell that endogenously comprises a TERT gene, e.g. for enhancing expression of hTERT in a normal human cell in which TERT expression is repressed. The target cell of these applications is, in many instances, a normal cell, e.g. a somatic cell. Expression of the TERT gene is considered to be enhanced if, consistent with the above description, expression is increased by at least about 2-fold, usually at least about 5-fold and often at least about 25-, about 50-, about 100-fold, about 300-fold or higher, as compared to a control, e.g., an otherwise identical cell not subjected to the subject methods, or becomes detectable from an initially undetectable state, as described above.

A more specific application in which the subject methods find use is to increase the proliferative capacity of a cell. The term "proliferative capacity" as used herein refers to the number of divisions that a cell can undergo, and preferably to the ability of the target cell to continue to divide where the daughter cells of such divisions are not transformed, i.e., they maintain normal response to growth and cell cycle regulation. The subject methods typically result in an increase in proliferative capacity of at least about 1.2-2 fold, usually at least about 5 fold and often at least about 10, 20, 50 fold or even higher, compared to a control. As such, yet another more specific application in which the subject methods find use is in the delay of the occurrence of cellular senescence. By practicing the subject methods, the onset of cellular senescence may be delayed by a factor of at least about 1.2-2 fold, usually at least about 5 fold and often at least about 10, 20, 50 fold or even higher, compared to a control.

Methods of Inhibiting TERT Expression

As mentioned above, also provided are methods for inhibiting TERT expression, e.g., by enhancing GC-Box 5 repression of TERT expression and thereby inhibiting TERT expression. In such methods, the amount and/or activity of the GC-Box 5 repressor protein is increased so as to enhance GC-Box 5 repressor mediated repression of TERT expression. A variety of different protocols may be employed to achieve this result, including administration of an effective amount of the GC-Box 5 repressor protein or analog/mimetic thereof, an agent that enhances expression of the target repressor protein or an agent that enhances the activity of the GC-Box. 5 repressor protein.

As such, the nucleic acid compositions that encode the GC-Box 5 repressor protein find use in situations where one wishes to enhance the activity of the repressor protein in a host. The repressor protein genes, gene fragments, or the encoded proteins or protein fragments are useful in gene therapy to treat disorders in which inhibition of TERT expression is desired, including those applications described in greater detail below. Expression vectors may be used to introduce the gene into a cell. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day, more usually for a period of at least about several days to several weeks.

The gene or protein may be introduced into tissues or host cells by any number of routes, including viral infection, microinjection, or fusion of vesicles. Jet injection may also be used for intramuscular administration, as described by Furth et al. (1992), Anal Biochem 205:365-368. The DNA may be coated onto gold microparticles, and delivered intradermally by a particle bombardment device, or "gene gun" as described in the literature (see, for example, Tang et al. (1992), Nature 356:152-154), where gold microprojectiles are coated with the DNA, then bombarded into skin cells.

Therapeutic Applications of TERT Expression Modulation

The methods find use in a variety of therapeutic applications in which it is desired to modulate, e.g., increase or decrease, TERT expression in a target cell or collection of cells, where the collection of cells may be a whole animal or portion thereof, e.g., tissue, organ, etc. As such, the target cell(s) may be a host animal or portion thereof, or may be a therapeutic cell (or cells) which is to be introduced into a multicellular organism, e.g., a cell employed in gene therapy. In such methods, an effective amount of an active agent that modulates TERT expression, e.g., enhances or decreases TERT expression as desired, is administered to the target cell or cells, e.g., by contacting the cells with the agent, by administering the agent to the animal, etc. By effective amount is meant a dosage sufficient to modulate TERT expression in the target cell(s), as desired.

In the subject methods, the active agent(s) may be administered to the targeted cells using any convenient means capable of resulting in the desired enhancement of TERT expression. Thus, the agent can be incorporated into a variety of formulations for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments (e.g., skin creams), solutions, suppositories, injections, inhalants and aerosols. As such, administration of the agents can be achieved in various ways, including oral, buccal, rectal, parenteral, intraperitoneal, intradermal, transdermal, intracheal, etc., administration.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Where the agent is a polypeptide, polynucleotide, analog or mimetic thereof, e.g. oligonucleotide decoy, it may be introduced into tissues or host cells by any number of routes, including viral infection, microinjection, or fusion of vesicles. Jet injection may also be used for intramuscular administration, as described by Furth et al. (1992), *Anal Biochem* 205:365-368. The DNA may be coated onto gold microparticles, and delivered intradermally by a particle bombardment device, or "gene gun" as described in the literature (see, for example, Tang et a. (1992), *Nature* 356:152-154), where gold microprojectiles are coated with the DNA, then bombarded into skin cells. For nucleic acid therapeutic agents, a number of different delivery vehicles find use, including viral and non-viral vector systems, as are known in the art.

Those of skill in the art will readily appreciate that dose levels can vary as a function of the specific compound, the nature of the delivery vehicle, and the like. Preferred dosages for a given compound are readily determinable by those of skill in the art by a variety of means.

The subject methods find use in the treatment of a variety of different conditions in which the enhancement of TERT expression in the host is desired. By treatment is meant that at least an amelioration of the symptoms associated with the condition afflicting the host is achieved, where amelioration is used in a broad sense to refer to at least a reduction in the magnitude of a parameter, e.g. symptom (such as inflammation), associated with the condition being treated. As such, treatment also includes situations where the pathological condition, or at least symptoms associated therewith, are completely inhibited, e.g. prevented from happening, or stopped, e.g. terminated, such that the host no longer suffers from the condition, or at least the symptoms that characterize the condition.

A variety of hosts are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

As indicated above, the subject invention provides methods of treating disease conditions resulting from a lack of TERT expression and methods of treating disease conditions resulting from unwanted TERT expression. Representative disease conditions for each category are now described in greater detail separately.

Treatment of Disease Conditions by Increasing TERT Expression

One representative disease condition that may be treated according to the subject invention is Progeria, or Hutchinson-Gilford syndrome. This condition is a disease of shortened telomeres for which no known cure exists. It afflicts children, who seldom live past their early twenties. In many ways progeria parallels aging itself. However, these children are born with short telomeres. Their telomeres don't shorten at a faster rate; they are just short to begin with. The subject methods can be used in such conditions to further delay natural telomeric shortening and/or increase telomeric length, thereby treating this condition.

Another specific disease condition in which the subject methods find use is in immune senescence. The effectiveness of the immune system decreases with age. Part of this decline is due to fewer T-lymphocytes in the system, a result of lost replicative capacity. Many of the remaining T-lymphocytes experience loss of function as their telomeres shorten and they approach senescence. The subject methods can be employed to inhibit immune senescence due to telomere loss. Because hosts with aging immune systems are at greater risk of developing pneumonia, cellulitis, influenza, and many other infections, the subject methods reduce morbidity and mortality due to infections.

The subject methods also find use in AIDS therapy. HIV, the virus that causes AIDS, invades white blood cells, particularly CD4 lymphocyte cells, and causes them to reproduce high numbers of the HIV virus, ultimately killing cells. In response to the loss of immune cells (typically about a billion per day), the body produces more CD8 cells to be able to suppress infection. This rapid cell division accelerates telomere shortening, ultimately hastening immune senescence of the CD8 cells. Anti-retroviral therapies have successfully restored the immune systems of AIDS patients, but survival depends upon the remaining fraction of the patient's aged T-cells. Once shortened, telomere length has not been naturally restored within cells. The subject methods can be employed to restore this length and/or prevent further shortening. As such the subject methods can spare telomeres and is useful in conjunction with the anti-retroviral treatments currently available for HIV.

Yet another type of disease condition in which the subject methods find use is cardiovascular disease. The subject methods can be employed to extend telomere length and replicative capacity of endothelial cells lining blood vessel walls (DeBono, Heart 80:110-1, 1998). Endothelial cells form the inner lining of blood vessels and divide and replace themselves in response to stress. Stresses include high blood pressure, excess cholesterol, inflammation, and flow stresses at forks in vessels. As endothelial cells age and can no longer divide sufficiently to replace lost cells, areas under the endothelial layer become exposed. Exposure of the underlying vessel wall increases inflammation, the growth of smooth muscle cells, and the deposition of cholesterol. As a result, the vessel narrows and becomes scarred and irregular, which contributes to even more stress on the vessel (Cooper, Cooke and Dzau, *J Gerontol Biol Sci* 49: 191-6, 1994). Aging endothelial cells also produce altered amounts of trophic factors (hormones that affect the activity of neighboring cells). These too contribute to increased clotting, proliferation of smooth muscle cells, invasion by white blood cells, accumulation of cholesterol, and other changes, many of which lead to plaque formation and clinical cardiovascular disease (Ibid.). By extending endothelial cell telomeres, the subject methods can be employed to combat the stresses contributing to vessel disease. Many heart attacks may be prevented if endothelial cells were enabled to continue to divide normally and better maintain cardiac vessels. The occurrence of strokes caused by the aging of brain blood vessels may also be significantly reduced by employing the subject methods to help endothelial cells in the brain blood vessels to continue to divide and perform their intended function.

The subject methods also find use in skin rejuvenation. The skin is the first line of defense of the immune system and shows the most visible signs of aging (West, Arch Dermatol 130(1):87-95, 1994). As skin ages, it thins, develops wrinkles, discolors, and heals poorly. Skin cells divide quickly in response to stress and trauma; but, over time, there are fewer and fewer actively dividing skin cells. Compounding the loss of replicative capacity in aging skin is a corresponding loss of support tissues. The number of blood vessels in the skin decreases with age, reducing the nutrients that reach the skin. Also, aged immune cells less effectively fight infection. Nerve cells have fewer branches, slowing the response to pain and increasing the chance of trauma. In aged skin, there are also fewer fat cells, increasing susceptibility to cold and temperature changes. Old skin cells respond more slowly and less accurately to external signals. They produce less vitamin D, collagen, and elastin, allowing the extracellular matrix to deteriorate. As skin thins and loses pigment with age, more ultraviolet light penetrates and damages skin. To repair the increasing ultraviolet damage, skin cells need to divide to replace damaged cells, but aged skin cells have shorter telomeres and are less capable of dividing (Fossel, REVERSING HUMAN AGING. William Morrow & Company, New York City, 1996).

By practicing the subject methods, e.g., via administration of an active agent topically, one can extend telomere length, and slow the downward spiral that skin experiences with age. Such a product not only helps protect a person against the impairments of aging skin; it also permits rejuvenated skin cells to restore youthful immune resistance and appearance. The subject methods can be used for both medical and cosmetic skin rejuvenation applications.

Yet another disease condition in which the subject methods find use in the treatment of osteoporosis. Two types of cells interplay in osteoporosis: osteoblasts make bone and osteoclasts destroy it. Normally, the two are in balance and maintain a constant turnover of highly structured bone. In youth, bones are resilient, harder to break, and heal quickly. In old age, bones are brittle, break easily, and heal slowly and often improperly. Bone loss has been postulated to occur because aged osteoblasts, having lost much of their replicative capacity, cannot continue to divide at the rate necessary to maintain balance (Hazzard et al. PRINCIPLES OF GERIATRIC MEDICINE AND GERONTOLOGY, 2d ed. McGraw-Hill, New York City, 1994). The subject methods can be employed to lengthen telomeres of osteoblast and osteoclast stem cells, thereby encouraging bone replacement and proper remodeling and reinforcement. The resultant stronger bone improves the quality of life for the many sufferers of osteoporosis and provides savings from fewer fracture treatments. The subject methods are generally part of a comprehensive treatment regime that also includes calcium, estrogen, and exercise.

Additional disease conditions in which the subject methods find use are described in WO 99/35243, the disclosures of which are herein incorporated by reference.

In addition to the above described methods, the subject methods can also be used to extend the lifetime of a mammal. By extend the lifetime is meant to increase the time during which the animal is alive, where the increase is generally at least 1%, usually at least 5% and more usually at least about 10%, as compared to a control.

As indicated above, instead of a multicellular animal, the target may be a cell or population of cells which are treated according to the subject methods and then introduced into a multicellular organism for therapeutic effect. For example, the subject methods may be employed in bone marrow transplants for the treatment of cancer and skin grafts for burn victims. In these cases, cells are isolated from a human donor and then cultured for transplantation back into human recipients. During the cell culturing, the cells normally age and senesce, decreasing their useful lifespans. Bone marrow cells, for instance, lose approximately 40% of their replicative capacity during culturing. This problem is aggravated when the cells are first genetically engineered (Decary, Mouly et al. Hum Gene Ther 7(11): 1347-50, 1996). In such cases, the therapeutic cells must be expanded from a single engineered cell. By the time there are sufficient cells for transplantation, the cells have undergone the equivalent of 50 years of aging (Decary, Mouly et al. Hum Gene Ther 8(12): 1429-38, 1997). Use of the subject methods spares the replicative capacity of bone marrow cells and skin cells during culturing and expansion and thus significantly improves the survival and effectiveness of bone marrow and skin cell transplants. Any transplantation technology requiring cell culturing can benefit from the subject methods, including ex vivo gene therapy applications in which cells are cultured outside of the animal and then administered to the animal, as described in U.S. Pat. Nos. 6,068,837; 6,027,488; 5,824,655; 5,821,235; 5,770,580; 5,756,283; 5,665,350; the disclosures of which are herein incorporated by reference.

Treatment of Disease Conditions by Decreasing TERT Expression

As summarized above, also provided are methods for enhancing repression of TERT expression, where by enhancement of TERT expression repression is meant a decrease in TERT expression by a factor of at least about 2-fold, usually at least about 5-fold and more usually at least about 10-fold, as compared to a control. Methods for enhancing GC-Box 5 mediated repression of TERT expression find use in, among other applications, the treatment of cellular proliferative disease conditions, particularly abnormal cellular proliferative disease conditions, including, but not limited to, neoplastic disease conditions, e.g., cancer. In such applications, an effective amount of an active agent, e.g., a GC-Box 5 repressor protein, analog or mimetic thereof, a vector encoding a GC-Box 5 repressor protein or active fragment thereof, an agent that enhances endogenous GC-Box 5 repressor activity, an agent that enhances expression of GC-Box 5 repressor protein, etc., is administered to the subject in need thereof. Treatment is used broadly as defined above, e.g., to include at least an amelioration in one or more of the symptoms of the disease, as well as a complete cessation thereof, as well as a reversal and/or complete removal of the disease condition, e.g., cure. Methods of treating disease conditions resulting from unwanted TERT expression, such as cancer and other diseases characterized by the presence of unwanted cellular proliferation, are described in, for example, U.S. Pat. Nos. 5,645,986; 5,656,638; 5,703,116; 5,760,062; 5,767,278; 5,770,613; and 5,863,936; the disclosures of which are herein incorporated by reference.

Nucleic Acid Compositions

Also provided by the subject invention are nucleic acid compositions, where the compositions are present in other than their natural environment, e.g., are isolated, recombinant, etc., that include a GC-Box 5 repressor binding site/domain/region, as described above. In other embodiments, the subject nucleic acids have a sequence that is substantially the same as, or identical to, the GC-Box 5 repressor binding site sequences as described above, e.g., SEQ ID NO: 01. A given sequence is considered to be substantially similar to this particular sequence if it shares high sequence similarity with the above described specific sequences, e.g. at least 75% sequence identity, usually at least 90%, more usually at least 95% sequence identity with the above specific sequences. Sequence similarity is calculated based on a reference sequence, which may be a subset of a larger sequence. Algorithms for sequence analysis are known in the art, such as BLAST, described in Altschul et al. (1990), *J. Mol. Biol.* 215:403-10 (using default settings, i.e. parameters w=4 and T=17). Of particular interest in certain embodiments are nucleic acids of substantially the same length as the specific nucleic acid identified above, where by substantially the same length is meant that any difference in length does not exceed about 20 number %, usually does not exceed about 10 number % and more usually does not exceed about 5 number %; and have sequence identity to this sequence of at least about 90%, usually at least about 95% and more usually at least about 99% over the entire length of the nucleic acid.

Also provided are nucleic acids that hybridize to the above-described nucleic acid under stringent conditions. An example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH7.6), 5× Denhardt's solution, 10% dextran sulfate, and 20 µg/ml denatured, sheared salmon sperm DNA, followed by washing the filters in 0.1×SSC at about 65° C. Stringent hybridization conditions are hybridization conditions that are at least as stringent as the above representative conditions, where conditions are considered to be at least as stringent if they are at least about 80% as stringent, typically at least about 90% as stringent as the above specific stringent conditions. Other stringent hybridization conditions are known in the art and may also be employed to identify nucleic acids of this particular embodiment of the invention.

In many embodiments, the above described nucleic acid compositions include the GC-Box 5 sequence/domain region but do not include the full sequence of the hTERT gene, or even minimal promoter thereof. In these embodiments, the subject nucleic acids include no more than about 90 number %, usually no more than about 80 number % and more usually no more than about 75 number %, where in many embodiments the subject nucleic acids include less than about 50 number %, sometimes less than about 40 number % and sometimes less than about 25 number % of the total sequence of the hTERT gene. In certain embodiments, the length of the subject nucleic acids ranges from about 5 to about 5000 bases, sometimes from about 10 to about 2500 bases and usually from about 10 to about 1000 bases, where in certain embodiments the length ranges from about 10 to about 500 bases, sometimes from about 10 to about 250 bases and sometimes from about 10 to about 100 bases, including from about 10 to about 50 bases.

The above-described nucleic acid compositions find use in a variety of different applications, including the preparation of constructs, e.g., vectors, expression systems, etc., as described more fully below, the preparation of probes for the GC-Box 5 repressor binding site sequence in non-human animals, i.e., non-human GC-Box 5 repressor binding site homologs, and the like. Where the subject nucleic acids are employed as probes, a fragment of the provided nucleic acid may be used as a hybridization probe against a genomic library from the target organism of interest, where low stringency conditions are used. The probe may be a large or small fragment, generally ranging in length from about 10 to 100 nt, usually from about 15 to 50 nt. Nucleic acids having sequence similarity are detected by hybridization under low stringency conditions, for example, at 50° C. and 6×SSC (0.9 M sodium chloride/0.09 M sodium citrate) and remain bound when subjected to washing at 55° C. in 1×SSC (0.15 M sodium chloride/0.015 M sodium citrate). Sequence identity may be determined by hybridization under stringent conditions, for example, at 50° C. or higher and 0.1×SSC (15 mM sodium chloride/01.5 mM sodium citrate). Nucleic acids having a region of substantial identity to the provided nucleic acid sequences bind to the provided sequences under stringent hybridization conditions. By using probes, particularly labeled probes of DNA sequences, one can isolate homologous or related sequences.

The subject nucleic acids are isolated and obtained in substantial purity, generally as other than an intact chromosome. As such, they are present in other than their naturally occurring environment. Usually, the DNA will be obtained substantially free of other nucleic acid sequences that do not include a GC-Box 5 repressor binding site sequence or fragment thereof, generally being at least about 50%, usually at least about 90% pure and are typically "recombinant", i.e. flanked by one or more nucleotides with which it is not normally associated on a naturally occurring chromosome.

The subject nucleic acids may be produced using any convenient protocol, including synthetic protocols, e.g., those where the nucleic acid is synthesized by a sequential monomeric approach (e.g., via phosphoramidite chemistry); where subparts of the nucleic acid are so synthesized and then assembled or concatamerized into the final nucleic acid, and the like. Where the nucleic acid of interest has a sequence that occurs in nature, the nucleic acid may be retrieved, isolated, amplified etc., from a natural source using conventional molecular biology protocols.

Also provided are nucleic acid compositions that include a modified or altered GC-Box 5 site, e.g., where the site includes one or more deletions or substitutions as compared to the above specific GC-Box 5 sequences, including a deletion or substitution of all or portion of the GC-Box 5 repressor binding site, e.g., including a deletion or substitution of at least one nucleotide, in certain embodiments at least four nucleotides within the GC-Box 5 region of nucleotides, and usually at least 7 nucleotides from this region, and sometimes all nucleotides from this region. Additionally, such a deletion may extend further, for example to include the nucleotides from positions outside of, e.g., from about 1 to about 20, including from about 1 to about 10, bp upstream or downstream, the above delineated GC-Box 5 regions, or subsets thereof. The subject nucleic acids of this embodiment that include a deletion (or substitution) in all or a portion of a GC-Box 5 repressor site of the TERT promoter may be present in the genome of a cell or animal of interest, e.g., as a "knockout" deletion in a transgenic cell or animal, where the cell or animal initially has this region, or may be present in an isolated form. A "knockout" animal could be produced from an animal that originally has the subject GC-Box 5 repressor site using the sequences flanking specific GC-Box 5 regions described here, e.g. as "homology clamps" and the basic "knockout" technology known to those skilled in the art e.g. see U.S. Pat. No. 5,464,764 to Capecchi, the disclosure of which is herein incorporated by reference.

Also provided are constructs comprising the subject nucleic acid compositions, e.g., those that include a GC-Box 5 repressor binding site or those that include a deletion in a GC-Box 5 repressor binding site, inserted into a vector, where such constructs may be used for a number of different applications, including propagation, screening, genome alteration, and the like, as described in greater detail below. Constructs made up of viral and non-viral vector sequences may be prepared and used, including plasmids, as desired. The choice of vector will depend on the particular application in which the nucleic acid is to be employed. Certain vectors are useful for amplifying and making large amounts of the desired DNA sequence. Other vectors are suitable for expression in cells in culture, e.g., for use in screening assays. Still other vectors are suitable for transfer and expression in cells in a whole animal or person. The choice of appropriate vector is well within the skill of the art. Many such vectors are available commercially. To prepare the constructs, the partial or full-length nucleic acid is inserted into a vector typically by means of DNA ligase attachment to a cleaved restriction enzyme site in the vector. Alternatively, the desired nucleotide sequence can be inserted by homologous recombination in vivo. Typically this is accomplished by attaching regions of homology to the vector on the flanks of the desired nucleotide sequence. Regions of homology are added by ligation of oligonucleotides, or by polymerase chain reaction using primers comprising both the region of homology and a portion of the desired nucleotide sequence, for example. Additional examples of nucleic acid compositions that include the GC-Box 5 repressor binding site are polymers, e.g. a double stranded DNA molecules, that mimic the GC-Box 5 repressor site as described above. Also of interest are anti-sense sequences which are sufficiently homologous to a GC-Box 5 binding site, such that they are useful to block attachment of the repressor protein to a GC-Box 5 repressor binding site.

Also provided are expression cassettes, vectors or systems that find use in, among other applications, screening for agents that modulate, e.g., inhibit or enhance the repressive activity of the region, as described in greater detail below; and/or to provide for expression of proteins under the control of the expression regulation mechanism of the TERT gene. By expression cassette or system is meant a nucleic acid that includes a sequence encoding a peptide or protein of interest, i.e., a coding sequence, operably linked to a promoter sequence, where by operably linked is meant that expression of the coding sequence is under the control of the promoter sequence. The expression systems and cassettes of the subject invention comprise a GC-Box 5 repressor binding site/region operably linked to the promoter, where the promoter is, in many embodiments, a TERT promoter, such as the hTERT promoter. See e.g., the hTERT promoter sequence described in Cong et al., Hum. Mol. Genet. (1999) 8:137-142.

As indicated above, expression systems comprising the subject regions find use in applications where it is desired to control expression of a particular coding sequence using the TERT transcriptional mechanism. In such applications, the expression system further includes the coding sequence of interest operably linked to the TERT promoter/GC-Box 5 repressor binding site elements. The expression system is then employed in an appropriate environment to provide expression or non-expression of the protein, as desired, e.g., in an environment in which telomerase is expressed, e.g., a Hela cell, or in an environment in which telomerase is not expressed, e.g., an MRC5 cell. Alternatively, the expression system may be used in an environment in which telomerase expression is inducible, e.g., by adding to the system an additional agent that turns on telomerase expression.

The above applications of the subject nucleic acid compositions are merely representative of the diverse applications in which the subject nucleic acid compositions find use.

Generation of Antibodies

Also provided are methods of generating antibodies, e.g., monoclonal antibodies. In one embodiment, the blocking or inhibition, either directly or indirectly as described above, of a GC-Box 5 repressor site/GC-Box 5 repressor interaction is used to immortalize cells in culture, e.g., by enhancing telomerase expression. Exemplary of cells that may be used for this purpose are non-transformed antibody producing cells, e.g. B cells and plasma cells which may be isolated and identified for their ability to produce a desired antibody using known technology as, for example, taught in U.S. Pat. No. 5,627,052. These cells may either secrete antibodies (antibody-secreting cells) or maintain antibodies on the surface of the cell without secretion into the cellular environment. Such cells have a limited lifespan in culture, and are usefully immortalized by upregulating expression of telomerase using the methods of the present invention.

Because the above-described methods are methods of increasing expression of TERT and therefore increasing the proliferative capacity and/or delaying the onset of senescence in a cell, they find applications in the production of a range of reagents, typically cellular or animal reagents. For example, the subject methods may be employed to increase proliferation capacity, delay senescence and/or extend the lifetimes of cultured cells. Cultured cell populations having enhanced TERT expression are produced using any of the protocols as described above, including by contact with an agent that inhibits repressor region transcription repression and/or modification of the repressor region in a manner such that it no longer represses TERT coding sequence transcription, etc.

The subject methods find use in the generation of monoclonal antibodies. An antibody-forming cell may be identified among antibody-forming cells obtained from an animal which has either been immunized with a selected substance, or which has developed an immune response to an antigen as a result of disease. Animals may be immunized with a selected antigen using any of the techniques well known in the art suitable for generating an immune response. Antigens may include any substance to which an antibody may be made, including, among others, proteins, carbohydrates, inorganic or organic molecules, and transition state analogs that resemble intermediates in an enzymatic process. Suitable antigens include, among others, biologically active proteins, hormones, cytokines, and their cell surface receptors, bacterial or parasitic cell membrane or purified components thereof, and viral antigens.

As will be appreciated by one of ordinary skill in the art, antigens which are of low immunogenicity may be accompanied with an adjuvant or hapten in order to increase the immune response (for example, complete or incomplete Freund's adjuvant) or with a carrier such as keyhole limpet hemocyanin (KLH).

Procedures for immunizing animals are well known in the art. Briefly, animals are injected with the selected antigen against which it is desired to raise antibodies. The selected antigen may be accompanied by an adjuvant or hapten, as discussed above, in order to further increase the immune response. Usually the substance is injected into the peritoneal cavity, beneath the skin, or into the muscles or bloodstream. The injection is repeated at varying intervals and the immune response is usually monitored by detecting antibodies in the serum using an appropriate assay that detects the properties of the desired antibody. Large numbers of antibody-forming cells can be found in the spleen and lymph node of the immunized animal. Thus, once an immune response has been generated, the animal is sacrificed, the spleen and lymph nodes are removed, and a single cell suspension is prepared using techniques well known in the art.

Antibody-forming cells may also be obtained from a subject which has generated the cells during the course of a selected disease. For instance, antibody-forming cells from a human with a disease of unknown cause, such as rheumatoid arthritis, may be obtained and used in an effort to identify antibodies which have an effect on the disease process or which may lead to identification of an etiological agent or body component that is involved in the cause of the disease. Similarly, antibody-forming cells may be obtained from subjects with disease due to known etiological agents such as malaria or AIDS. These antibody forming cells may be derived from the blood or lymph nodes, as well as from other diseased or normal tissues. Antibody-forming cells may be prepared from blood collected with an anticoagulant such as heparin or EDTA. The antibody-forming cells may be further separated from erythrocytes and polymorphs using standard procedures such as centrifugation with Ficoll-Hypaque (Pharmacia, Uppsula, Sweden). Antibody-forming cells may also be prepared from solid tissues such as lymph nodes or tumors by dissociation with enzymes such as collagenase and trypsin in the presence of EDTA.

Antibody-forming cells may also be obtained by culture techniques such as in vitro immunization. Briefly, a source of antibody-forming cells, such as a suspension of spleen or lymph node cells, or peripheral blood mononuclear cells are cultured in medium such as RPMI 1640 with 10% fetal bovine serum and a source of the substance against which it is desired to develop antibodies. This medium may be additionally supplemented with amounts of substances known to enhance antibody-forming cell activation and proliferation such as lipopolysaccharide or its derivatives or other bacterial adjuvants or cytokines such as IL-1, IL-2, IL-4, IL5, IL-6, GM-CSF, and IFN-.gamma. To enhance immunogenicity, the selected antigen may be coupled to the surface of cells, for example, spleen cells, by conventional techniques such as the use of biotin/avidin as described below.

Antibody-forming cells may be enriched by methods based upon the size or density of the antibody-forming cells relative to other cells. Gradients of varying density of solutions of bovine serum albumin can also be used to separate cells according to density. The fraction that is most enriched for desired antibody-forming cells can be determined in a preliminary procedure using the appropriate indicator system in order to establish the antibody-forming cells.

The identification and culture of antibody producing cells of interest is followed by enhancement of TERT expression in these cells by the subject methods, thereby avoiding the need for the immortalization/fusing step employed in traditional hybridoma manufacture protocols. In such methods, the first step is immunization of the host animal with an immunogen, typically a polypeptide, where the polypeptide will preferably be in substantially pure form, comprising less than about 1% contaminant. The immunogen may comprise the complete protein, fragments or derivatives thereof. To increase the immune response of the host animal, the protein may be combined with an adjuvant, where suitable adjuvants include alum, dextran sulfate, large polymeric anions, oil & water emulsions, e.g. Freund's adjuvant, Freund's complete adjuvant, and the like. The protein may also be conjugated to synthetic carrier proteins or synthetic antigens. A variety of hosts may be immunized to produce the subject antibodies. Such hosts include rabbits, guinea pigs, rodents (e.g. mice, rats), sheep, goats, and the like. The protein is administered to the host, usually intradermally, with an initial dosage followed by one or more, usually at least two, additional booster dosages. Following immunization, generally, the spleen and/or lymph nodes of an immunized host animal provide a source of plasma cells. The plasma cells are treated according to the subject invention to enhance TERT expression and thereby, increase the proliferative capacity and/or delay senescence to produce "pseudo" immortalized cells. Culture supernatant from individual cells is then screened using standard techniques to identify those producing antibodies with the desired specificity. Suitable animals for production of monoclonal antibodies to a human protein include mouse, rat, hamster, etc. To raise antibodies against the mouse protein, the animal will generally be a hamster, guinea pig, rabbit, etc. The antibody may be purified from the cell supernatants or ascites fluid by conventional techniques, e.g. affinity chromatography using RFLAT-1 protein bound to an insoluble support, protein A sepharose, etc.

In an analogous fashion, the subject methods are employed to enhance TERT expression in non-human animals, e.g., non-human animals employed in laboratory research. Using the subject methods with such animals can provide a number of advantages, including extending the lifetime of difficult and/or expensive to produce transgenic animals. As with the above-described cells and cultures thereof, the expression of TERT in the target animals may be enhanced using a number of different protocols, including the administration of an agent that inhibits GC-Box 5 repressor protein repression and/or targeted disruption of the GC-Box 5 repressor binding site. The subject methods may be used with a number of different types of animals, where animals of particular interest include mammals, e.g., rodents such as mice and rats, cats, dogs, sheep, rabbits, pigs, cows, horses, and non-human primates, e.g. monkeys, baboons, etc.

Screening Assays

Also provided by the subject invention are screening protocols and assays for identifying agents that modulate, e.g., inhibit or enhance, GC-Box 5 repression of TERT transcription. The screening methods include assays that provide for qualitative/quantitative measurements of TERT promoter controlled expression, e.g., of a coding sequence for a marker or reporter gene, in the presence of a particular candidate therapeutic agent. Assays of interest include assays that measures the TERT promoter controlled expression of a reporter gene (i.e. coding sequence, e.g., luciferase, SEAP, etc.) in the presence and absence of a candidate inhibitor agent, e.g., the expression of the reporter gene in the presence or absence of a candidate agent. The screening method may be an in vitro or in vivo format, where both formats are readily developed by those of skill in the art. Whether the format is in vivo or in vitro, an expression system, e.g., a plasmid, that includes a GC-Box 5 repressor binding site, a TERT promoter and a reporter coding sequence all operably linked is combined with the candidate agent in an environment in which, in the absence of the candidate agent, the TERT promoter is repressed, e.g., an expression system in which the presence of the repressor protein that interacts with the GC-Box 5 repressor binding site causes TERT promoter repression. The conditions may be set up in vitro by combining the various required components in an aqueous medium, or the assay may be carried out in vivo, e.g., in a cell that normally lacks telomerase activity, e.g., an MRC5 cell, etc.

A variety of different candidate agents may be screened by the above methods. Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Agents identified in the above screening assays that inhibit GC-Box 5 repression of TERT transcription find use in the methods described above, e.g., in the enhancement of TERT expression. Alternatively, agents identified in the above screening assays that enhance GC-Box 5 repression find use in applications where inhibition of TERT expression is desired, e.g., in the treatment of disease conditions characterized by the presence of unwanted TERT expression, such as cancer and other diseases characterized by the presence of unwanted cellular proliferation, where such methods are described in, for example, U.S. Pat. Nos. 5,645,986; 5,656,638; 5,703,116; 5,760,062; 5,767,278; 5,770,613; and 5,863,936; the disclosures of which are herein incorporated by reference.

The following examples are offered by way of illustration and not by way of limitation.

EXPERIMENTAL

Example 1

To identify bases that make up the repressor site, deletions were made in the telomerase minimal promoter (FIG. 1). Each deletion is 10 bases long with 7 to 8 base overlaps between consecutive deletions. The deletions were made in the minimal telomerase promoter in the plasmid designated pSSI20 (the full anotated sequence of pSSI20 is provided in FIG. 2 of the Site C patent) (Do we need to show this again or can we just reference the Site C patent?). Each deletion mutant was independently made three times and all deletions were transiently transfected into MRC5 (telomerase negative normal cells) and HELA (telomerase positive immortal cells).

Of particular interest are sequences with a deletion extending from −87 to ~0, comprising the nucleotides GCCCCGCC which make up the central core of a consensus GC Box (i.e. GC Box 5) found between bases ~9 to −76 (SEQ ID NO:01; i.e. CGGCCCCGCCCTCT), The expression levels were measured using the Secreted Alkaline Phosphatase Assay (SEAP Assay) commercially available from Clontech (Palo Alto, Calif.). The results are shown below.

| Deletion | MRC5 |
|---|---|
| NONE (control) | 0.1931 |
| −104 to −95 | 0.19 |
| −102 to −93 | 4.92 |
| −99 to −90 | 1.19 |
| −97 to −88 | 1.69 |
| −94 to −85 | 8.06 |
| −92 to −83 | 7.89 |
| −89 to −80 | 12.00 |
| −87 to −78 | 7.26 |
| −84 to −75 | 7.77 |
| −82 to −73 | 4.83 |
| −79 to −70 | 3.79 |
| −77 to −68 | 17.15 |
| −74 to −65 | 34.44 |
| −72 to −63 | 33.22 |
| −69 to −60 | 33.15 |
| −67 to −58 | 56.98 |
| −64 to −55 | 21.82 |
| −62 to −53 | 4.60 |
| −59 to −50 | 19.58 |

The column of deletions indicates the bases that were deleted in the repressor site, which is indicated relative to the AUG start codon. The column for MRC5 shows the level of expression observed for each deletion, reported as a percentage of the SV40 early promoter, which was used to normalize the two cell lines.

The data demonstrate that the deletions from "−94 to −85, −92 to −83, −89 to −80, −87 to −78, −84 to −75, −82 to −73, and −79 to −70" gave significantly higher SEAP readings, as compared to the control cells with no deletion in the promoter. This indicates that a repressor function operates in MRC5 cells to repress expression of the wild type telomerase promoter.

Example 2

The mutation 80. C→A causes a 2.5 fold increase in expression in MCR5 suggesting that GCBox 5 is a repressor site. This data is shown below:

MRC5

| Promoter | Mutations | SEAP Scores | | | Average Score |
|---|---|---|---|---|---|
| MP | None | 791.7 | 591.2 | 556.7 | 646.53333 |
| MP | −80 C−>A | 1596 | 1568 | 1776 | 1646.6667 |

Example 3

Deletion of the sequences between GC Box 5 and Site C result in a 2.9 fold increase in expression in MRC5. This suggests that the GC Box 5 binding protein interacts with the Site C binding protein to cause repression of the telomerase promoter and deletion of the sequences between the binding sites interferes with their interaction.

MRC5

| Mutations | SEAP Scores | | | Average Score |
|---|---|---|---|---|
| None | 917.0 | 443.6 | 429.0 | 596.53333 |
| Deletion of −75 to −70 | 1593 | 2019 | 1611 | 1741 |

Example 4

Insertion of 1,2, or 3 A's between GC Box 5 and Site C causes a 1.2 to 2.0 fold increase in expression. This suggests that the GC Box 5 binding protein interacts with the Site C binding protein to cause repression of the telomerase minimal promoter and insertion of bases between the binding sites interferes with their interaction.

| Mutations | SEAP Scores | | | Average Score | Fold Increase |
|---|---|---|---|---|---|
| None | 785.3 | 911.8 | 1976 | 1224.3667 | |
| Insertion of 1 A between bases −73 and −72 | 3028 | 2071 | 1936 | 2345 | 1.915276 |
| Insertion of 2 A's between bases −73 and −72 | 1432 | 1846 | 1036 | 1438 | 1.174485 |
| Insertion of 3 A's between bases −73 and −72 | 2416 | 1623 | 3218 | 2419 | 1.975715 |

It is evident from the above results and discussion that the subject invention provides important new nucleic acid compositions that find use in a variety of applications, including the establishment of expression systems that exploit the regulatory mechanism of the TERT gene and the establishment of screening assays for agents that modulated, e.g., enhance or inhibit, TERT expression. In addition, the subject invention provides methods of enhancing TERT expression in a cellular or animal host, which methods find use in a variety of applications, including the production of scientific research reagents and therapeutic treatment applications. Accordingly, the subject invention represents significant contribution to the art.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

What is claimed is:

1. A method of determining whether an agent inhibits GC-Box 5 repression of TERT activity in cultured cells, said method comprising:
   (a) contacting said agent with a first expression system comprising a GC-Box 5 repressor binding site and a coding sequence operably linked to a TERT promoter under conditions such that in the absence of said agent transcription of said coding sequence is repressed as compared to transcription in the presence of said agent;
   (b) contacting said agent with a second expression system comprising said coding sequence operably linked to said TERT promoter, wherein said second expression system does not comprise said GC-Box 5 repressor binding site;
   wherein said first and second expression systems are cultured cells;
   (c) determining whether transcription of said coding sequence in said first expression system is repressed in the presence of said agent as compared to transcription in the absence of said agent;
   (d) determining whether transcription of said coding sequence in said second expression system is altered in the presence of said agent as compared to transcription in the absence of said agent; and
   (e) identifying said agent as an agent that inhibits GC-Box 5 repression of TERT transcription if transcription of said coding sequence in said first expression system is not repressed in the presence of said agent as compared to transcription in the absence of said agent and transcription of said coding sequence in said second expression system is not altered in the presence of said agent as compared to transcription in the absence of said agent.

2. The method according to claim 1, wherein said agent is a small molecule.

3. The method according to claim 1, wherein said cultured cells do not express telomerase.

4. The method according to claim 3, wherein said cultured cells are an MRC5 cells.

5. The method according to claim 1, wherein said coding sequence encodes a luciferase.

6. The method according to claim 1, wherein said coding sequence encodes a secreted alkaline phosphatase (SEAP).

7. The method according to claim 1, wherein said agent is a biomolecule.

8. The method according to claim 7, wherein said biomolecule is selected from the group consisting of peptides, proteins, nucleic acids, oligonucleotides, saccharides, fatty acids, steroids, purines, pyrimidines, and derivatices or structural analogs thereof.

9. The method according to claim 1, wherein each of said expression systems comprises a vector.

10. The method according to claim 9, wherein said vector is a plasmid.

11. The method according to claim 9, wherein the vector is a viral vector.

* * * * *

UNITED STATES PATENT AND TRADEMARK OFFICE
CERTIFICATE OF CORRECTION

| | | |
|---|---|---|
| PATENT NO. | : 7,279,328 B1 | Page 1 of 1 |
| APPLICATION NO. | : 10/826466 | |
| DATED | : October 9, 2007 | |
| INVENTOR(S) | : William H. Andrews et al. | |

It is certified that error appears in the above-identified patent and that said Letters Patent is hereby corrected as shown below:

Column 22, Line 69: Insert --Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.--.

Claim 8 line 50: Delete "derivatices" and replace it with "derivatives".

Signed and Sealed this
Twenty-sixth Day of April, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,279,328 B1 | Page 1 of 1 |
| APPLICATION NO. | : 10/826466 | |
| DATED | : October 9, 2007 | |
| INVENTOR(S) | : William H. Andrews et al. | |

It is certified that error appears in the above-identified patent and that said Letters Patent is hereby corrected as shown below:

Column 22, Line 69: Insert --Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.--.

Column 24, Claim 8, Line 50: Delete "derivatices" and replace it with "derivatives".

This certificate supersedes the Certificate of Correction issued April 26, 2011.

Signed and Sealed this
Twenty-fourth Day of May, 2011

David J. Kappos
*Director of the United States Patent and Trademark Office*

SEQUENCE LISTING

<160> NUMBER OF SEQ ID NOS: 2

<210> SEQ ID NO 1
<211> LENGTH: 14
<212> TYPE: DNA
<213> ORGANISM: human

<400> SEQUENCE: 1
cggccccgcc ctct                                                                14

<210> SEQ ID NO 2
<211> LENGTH: 295
<212> TYPE: DNA
<213> ORGANISM: HUMAN

<400> SEQUENCE: 2

```
cgcgtgctag cccgggctcg agccaggacc gcgctcccca cgtggcggag ggactgggga      60
cccgggcacc cgtcctgccc cttcaccttc cagctccgcc tcctccgcgc ggacccccgcc    120 ccgtcccgac ccctcccggg tccccggccc agccccctcc gggccctccc agccccctccc   180 cttcctttcc gcggccccgc cctctcctcg cggcgcgagt ttcaggcagc gctgcgtcct    240
gctgcgcacg tgggaagccc tggccccggc cacccccgcg aattcgccca ccatg         295
```